United States Patent
Marino et al.

(10) Patent No.: US 6,478,805 B1
(45) Date of Patent: Nov. 12, 2002

(54) SYSTEM FOR REMOVING CUT TISSUE FROM THE INNER BORE OF A SURGICAL INSTRUMENT

(75) Inventors: James F. Marino, La Jolla; Nicolei R. King, San Diego; Robert S. Lynch, San Diego; Corbett W. Stone, San Diego, all of CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/548,905

(22) Filed: Apr. 13, 2000

Related U.S. Application Data

(60) Provisional application No. 60/167,189, filed on Nov. 23, 1999, and provisional application No. 60/129,703, filed on Apr. 16, 1999.

(51) Int. Cl.[7] .............................................. A61B 17/32
(52) U.S. Cl. ..................................................... 606/170
(58) Field of Search ................................ 606/170, 171, 606/172, 184, 185, 177, 83, 110, 114, 115; 600/566, 567

(56) References Cited

U.S. PATENT DOCUMENTS

| | | | |
|---|---|---|---|
| 4,522,206 A | | 6/1985 | Whipple et al. |
| 4,678,459 A | | 7/1987 | Onik et al. |
| RE33,258 E | | 7/1990 | Onik et al. |
| 5,285,795 A | | 2/1994 | Ryan et al. |
| 5,423,330 A | | 6/1995 | Lee |
| 5,603,724 A | | 2/1997 | O'Connor |
| 5,702,420 A | | 12/1997 | Sterling et al. |
| 5,873,886 A | | 2/1999 | Larsen et al. |
| 5,879,365 A | | 3/1999 | Whitfield et al. |
| 5,947,983 A | * | 9/1999 | Solar et al. ............... 606/144 |

* cited by examiner

*Primary Examiner*—Michael J. Milano
*Assistant Examiner*—Vy Q. Bui
(74) *Attorney, Agent, or Firm*—Jonathan Spangler

(57) ABSTRACT

A system for removing cut tissue from the inner bore of a surgical rongeur or suction punch, comprising: an elongated tubular member having a side hole positioned adjacent its distal end; and an insert projecting inwardly from the distal end of the tubular member into the inner bore of the tubular member.

9 Claims, 10 Drawing Sheets

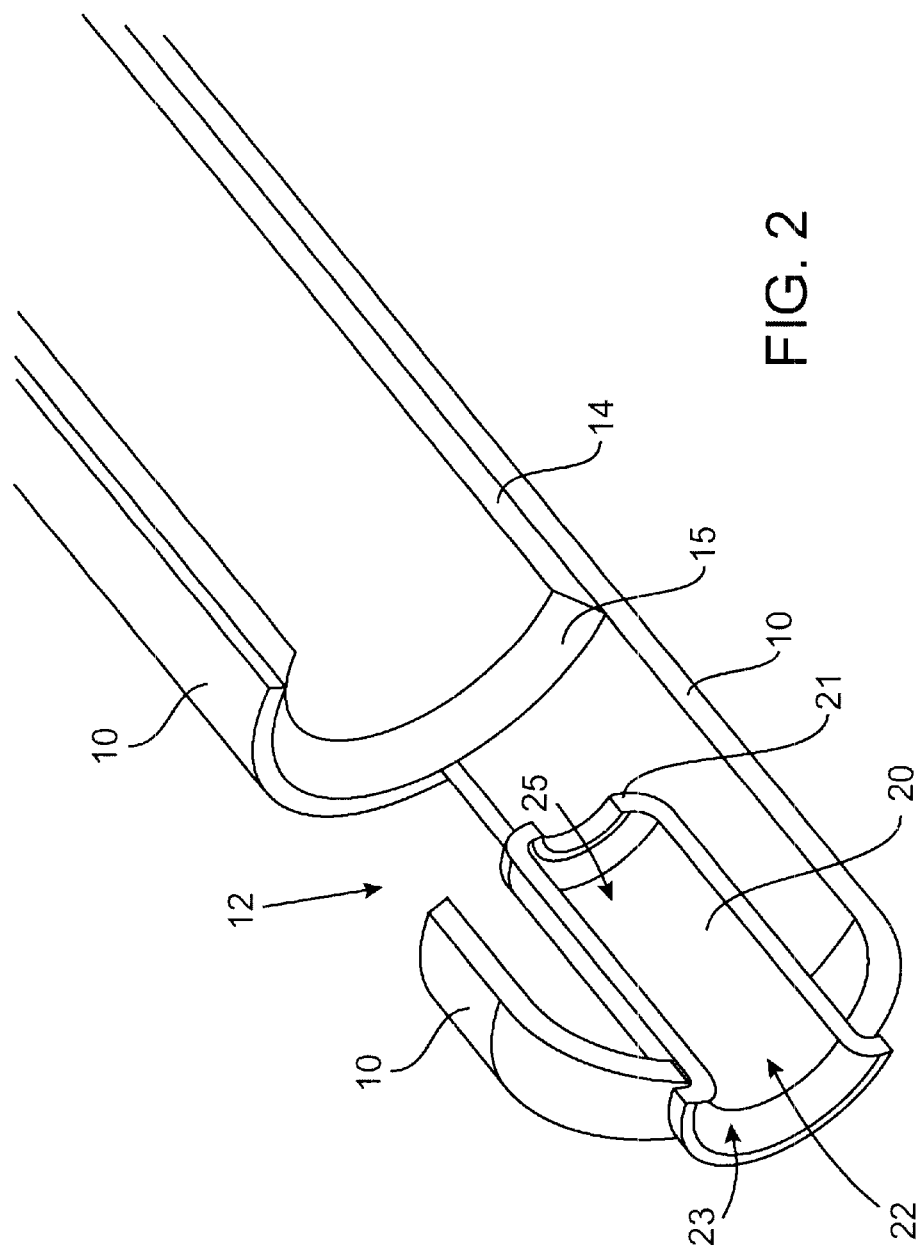

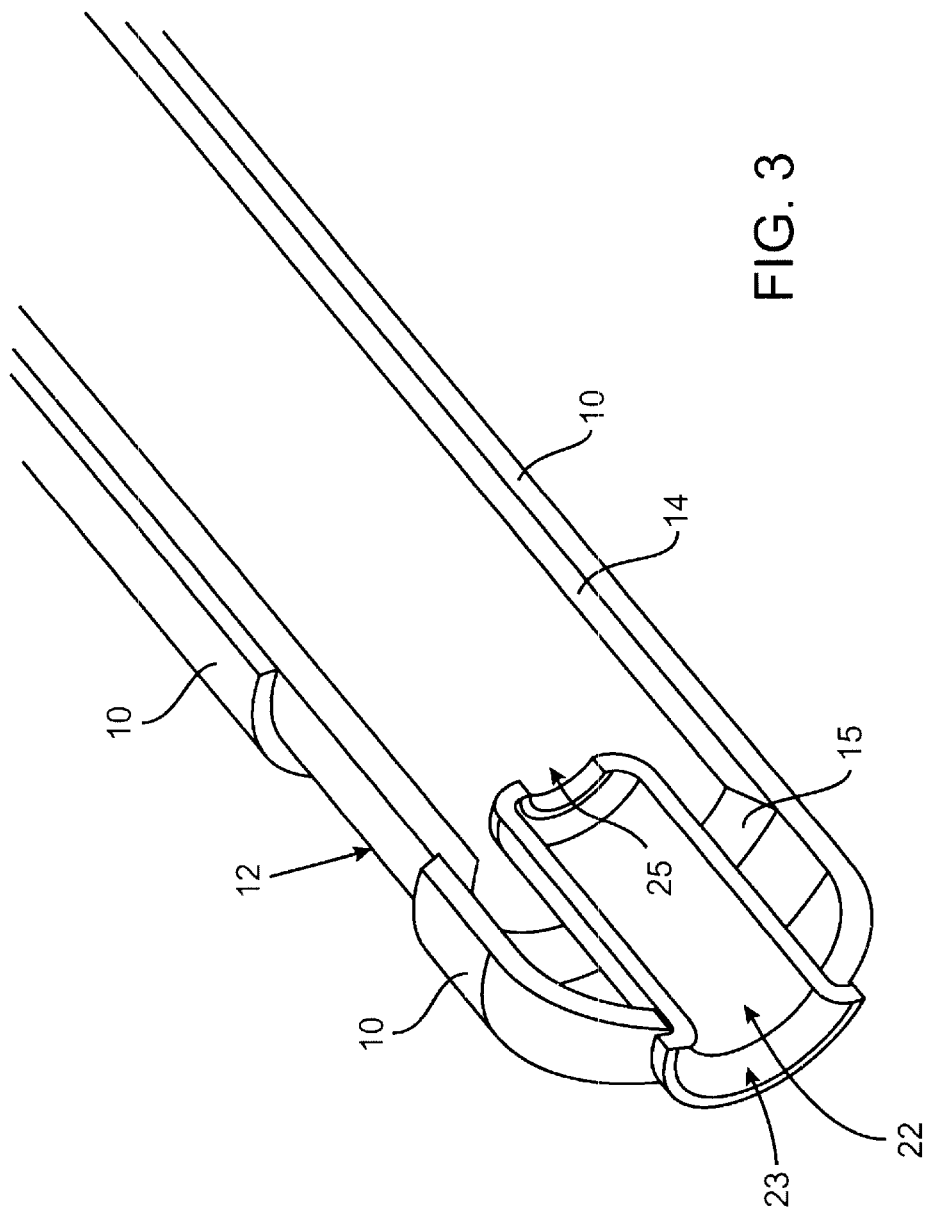

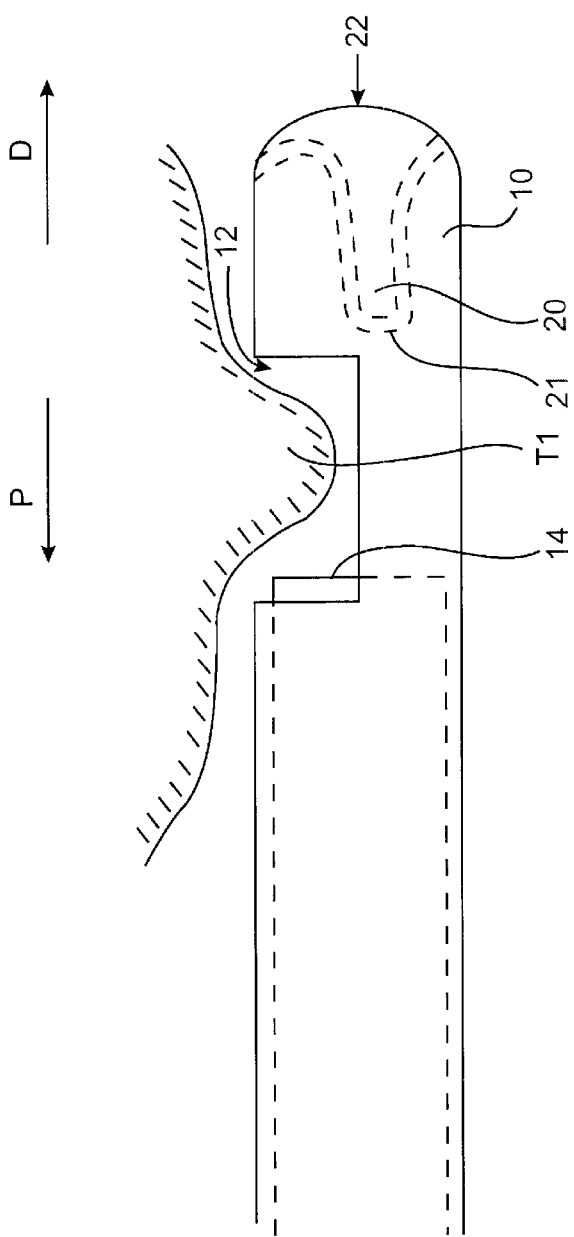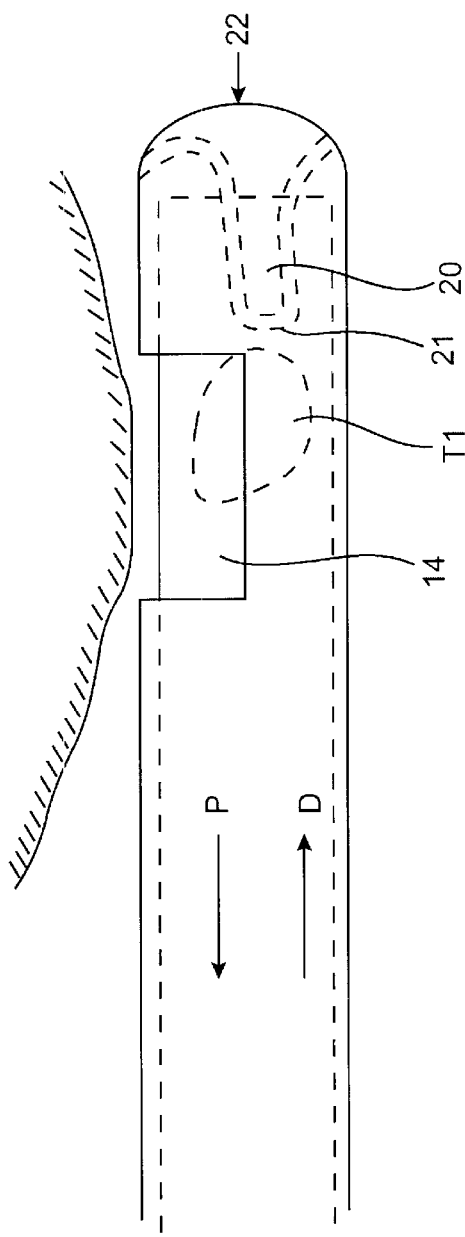

SYSTEM FOR REMOVING CUT TISSUE FROM THE INNER BORE OF A SURGICAL INSTRUMENT

CROSS-REFERENCES TO RELATED APPLICATIONS

The present application is a regular patent application of and claims the benefit of priority from U.S. Patent Application Ser. No. 60/167,189 filed Nov. 23, 1999 and No. 60/129,703 filed Apr. 16, 1999, the full disclosures of which are incorporated herein by reference.

TECHNICAL FIELD

The present invention relates to rongeurs and suction punches.

BACKGROUND OF THE INVENTION

Rongeurs and suction punches typically comprise a long tubular element having a small side opening near its distal end. A cutting element is operated to slide longitudinally back and forth within the inner bore of the tubular element. The cutting element is specifically adapted to cut away any tissues protruding inwardly through the side hole.

A problem with existing rongeurs and suction punches are that the cut away tissue tends to become compacted within inner bore of the tubular element, especially within the region adjacent the distal side hole.

Suction punches operate similar to rongeurs, but suction is maintained to draw the cut away tissue out of the inner bore of the tubular element. A problem common to existing suction punches in particular is that when the cutting element is advanced distally to cut away the portion of tissue projecting into the side hole, a vacuum is created within the inner bore of the suction punch, thus preventing tissue from easily being removed. As such, the cut away tissues are only removed when the cutting element is retracted, and the distal side hole is opened. Only when the side hole is opened, air and fluid may enter the side hole such that the cut tissues may be sucked out of the center tube of the suction punch.

SUMMARY OF THE INVENTION

The present invention provides a system for removing cut tissue from the inner bore of the tubular element of a surgical rongeur or suction punch. In preferred aspects, the tubular member is fitted with a member which projects inwardly from its distal end, (into the interior bore of the tubular member).

Preferably, this member projects inwardly to a distance such that a proximal end of the member is disposed adjacent the side hole cutting region of the rongeur/suction punch.

In further preferred aspects of the invention, the tubular member of the rongeur/suction punch has an orifice passing through its distal end to permit air and fluid flow therein. An advantage of permitting air and fluid flow in through the distal end of the tubular member is that a vacuum is not formed within the device. Rather, a steady suctioning of cut away tissues out of the inner bore of the device can be easily achieved.

In a preferred aspect of the invention, a hollow member which projects inwardly from the distal end of the rongeur/suction punch into the inner bore of the tubular member of the rongeur/suction punch is used to accomplish both the benefits of a member projecting inwardly from the distal end of the tubular member and an orifice passing air and fluid into the distal end of the tubular member. The hollow member may be an integral portion of an end tip of the device, or may alternatively comprise a tube inserted into the distal end of the device.

Systems are also provided for ensuring that tissue fibers are cleanly cut away by the device such that fibers do not become jammed in the device during its operation. In a preferred aspect, the system for cleanly cutting away tissue fibers comprises a flat surface against which the blade at the distal end of the tubular cutting element seats when the side opening in the device is closed, (i.e., when the cutting element fully extended in a distal direction).

BRIEF DESCRIPTION OF THE DRAWINGS

FIG. 2 is a sectional perspective view of the present invention in a fully opened "ready-to-cut" position.

FIG. 3 is a sectional elevation view of the present invention in a fully closed position.

FIG. 4 is a side elevation view of the present invention positioned ready to cut a mass of tissue.

FIG. 5 is a side elevation view showing a cut mass of tissue in phantom.

DESCRIPTION OF THE SPECIFIC EMBODIMENTS

Figure 1:
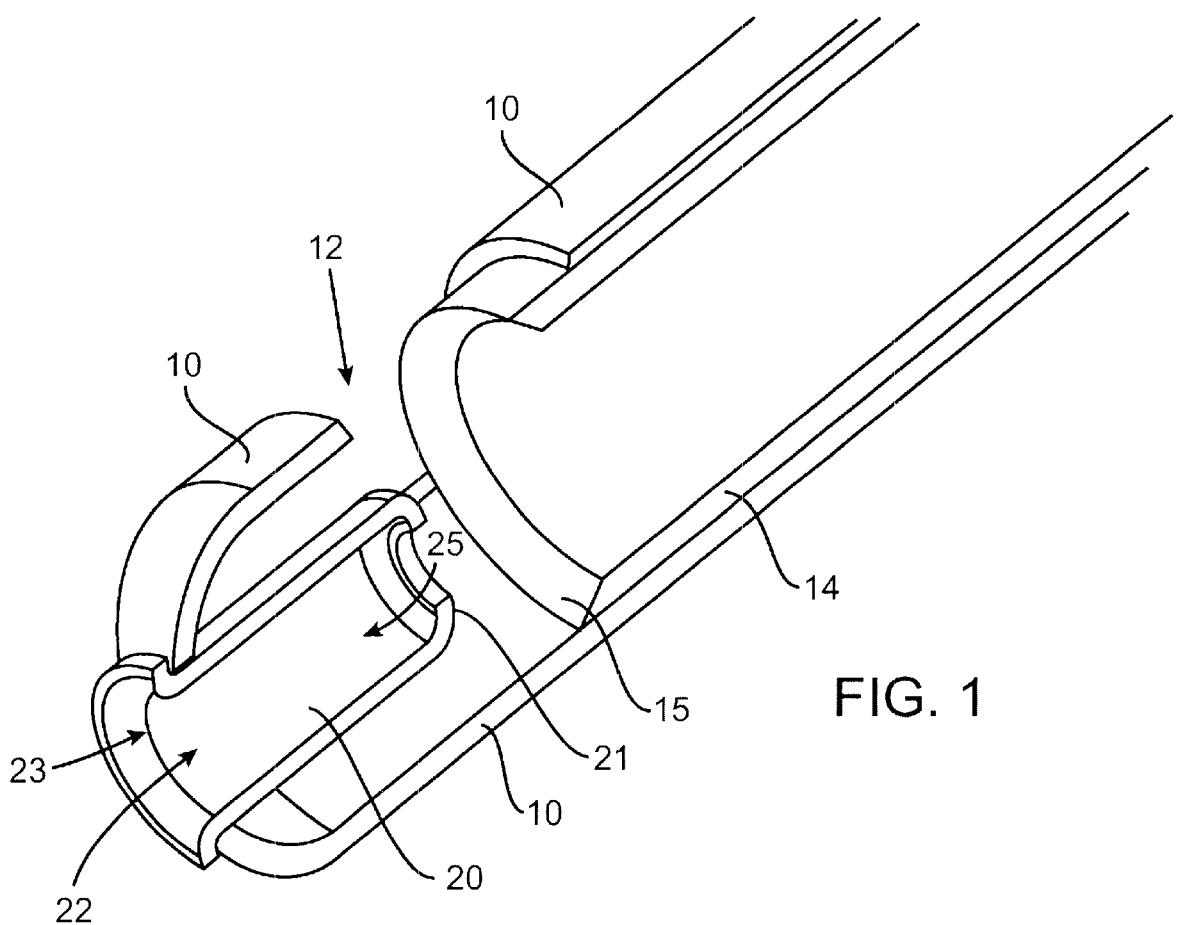
FIG. 1 is a sectional perspective view of the present invention in a partially opened position.

Referring to FIG. 1, the distal end of a surgical rongeur/suction punch is shown. Specifically, the surgical rongeur/suction punch comprises a tubular element 10 having a side opening 12. Within the interior bore of tubular element 10 is disposed a tubular cutting element 14 having a sharpened blade 15 at its distal end, typical of existing systems. Tissue is cut or resected by sliding tubular cutting element 14 in a distal direction from the position shown in FIG. 2 (in which side opening 12 is fully opened), to the position shown in FIG. 3, (in which side opening 12 is fully closed). During this procedure, a protruding tissue mass is pushed into side opening 12 such that it protrudes inwardly into the interior bore of tubular element 10.

The present invention provides an insert 20 which is received into an opening 22 in the distal end of tubular element 10. Insert 20 offers numerous advantages and provides a system for removing cut tissue from the inner bore of tubular element 14 as follows.

Figure 6:
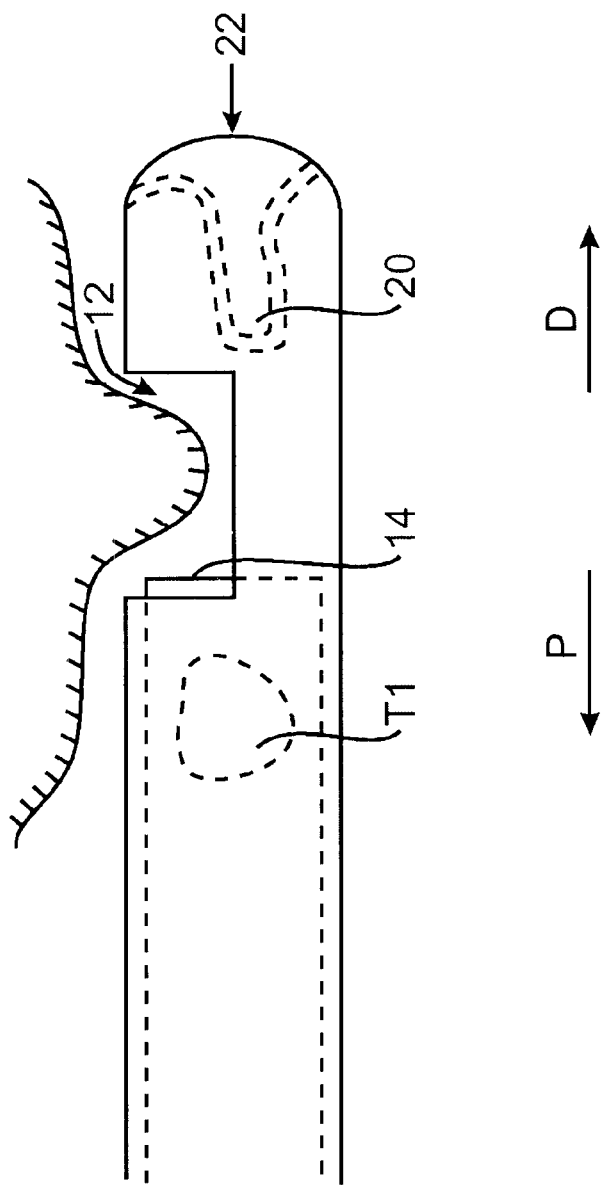
FIG. 6 is a side elevation view showing the present system in a open "ready-to-cut" position after previously cutting a tissue mass.

Referring to FIG. 4, a protruding mass of tissue T1 is inserted into side opening 12 when tubular element 14 is fully retracted (in the position as shown in FIG. 2). Advancement of tubular cutting element 14 to the position shown in FIG. 5 will sever tissue mass T1 such that it remains within the internal bore of tubular cutting element 14. As cutting blade 14 is advanced fully forward (in a distal direction) to the position shown in FIG. 5, insert 20, which protrudes into the bore of blade 14 from the distal end of tubular element 10, will push against tissue mass TI causing it to move in a proximal direction P within the inner bore of blade 14. As such when blade 14 is withdrawn, (in proximal direction P), to the position shown in FIG. 6, tissue mass T1 will be pushed upstream of side opening 12 as shown.

Accordingly, insert 20 offers the advantage both of helping to decompact cut tissue mass by pushing the tissue mass in a proximal direction when cutting blade 14 is advanced fully forward, and also in positioning the tissue masses behind and out of the way of side opening 12 when the cutting blade is retracted for further cutting. In a preferred aspect, insert 20 preferably has a flat face 21 at its proximal end.

As is seen in FIGS. 1–3, insert 20 may preferably comprise a hollow tube having a distal opening 23 and a proximal opening 25 permitting air and fluid flow therethrough. This feature of the invention offers the important advantage of "vacuum breaking" in which a steady suction can be maintained on the inner bore of blade 14, thereby continuously removing cut away tissues, as follows.

When blade 14 is advanced distally after cutting to the position shown in FIG. 3, such that side hole 12 is now closed, air and fluid flow into the interior tubular bore of blade 14 through openings 23 and 25 prevents a vacuum from building up in the interior of the device. As such, a steady suctioning of cut tissue from the interior bore of blade 14 can be achieved with the tissue being withdrawn from the interior bore of the device even though side opening 12 has been closed.

In another aspect of the invention, the combined effect of insert 20 physically moving cut tissue in proximal direction P when blade 14 is advanced in distal direction D while simultaneously permitting a suction flow into the interior bore of the device, operates to remove cut tissues from the rongeur/suction punch.

Preferably as well, insert 20 comprises a hollow tube having an inner bore diameter which is dimensioned to be narrow enough such that air and fluid passing therethrough prevents a vacuum from forming in the inner bore of the surgical rongeur or suction punch, yet is dimensioned to be wide enough such that a sufficient suction force can be maintained in the inner bore of the elongated tubular member.

A second embodiment of the invention is shown in FIGS. 7 to 11.

Figure 7:
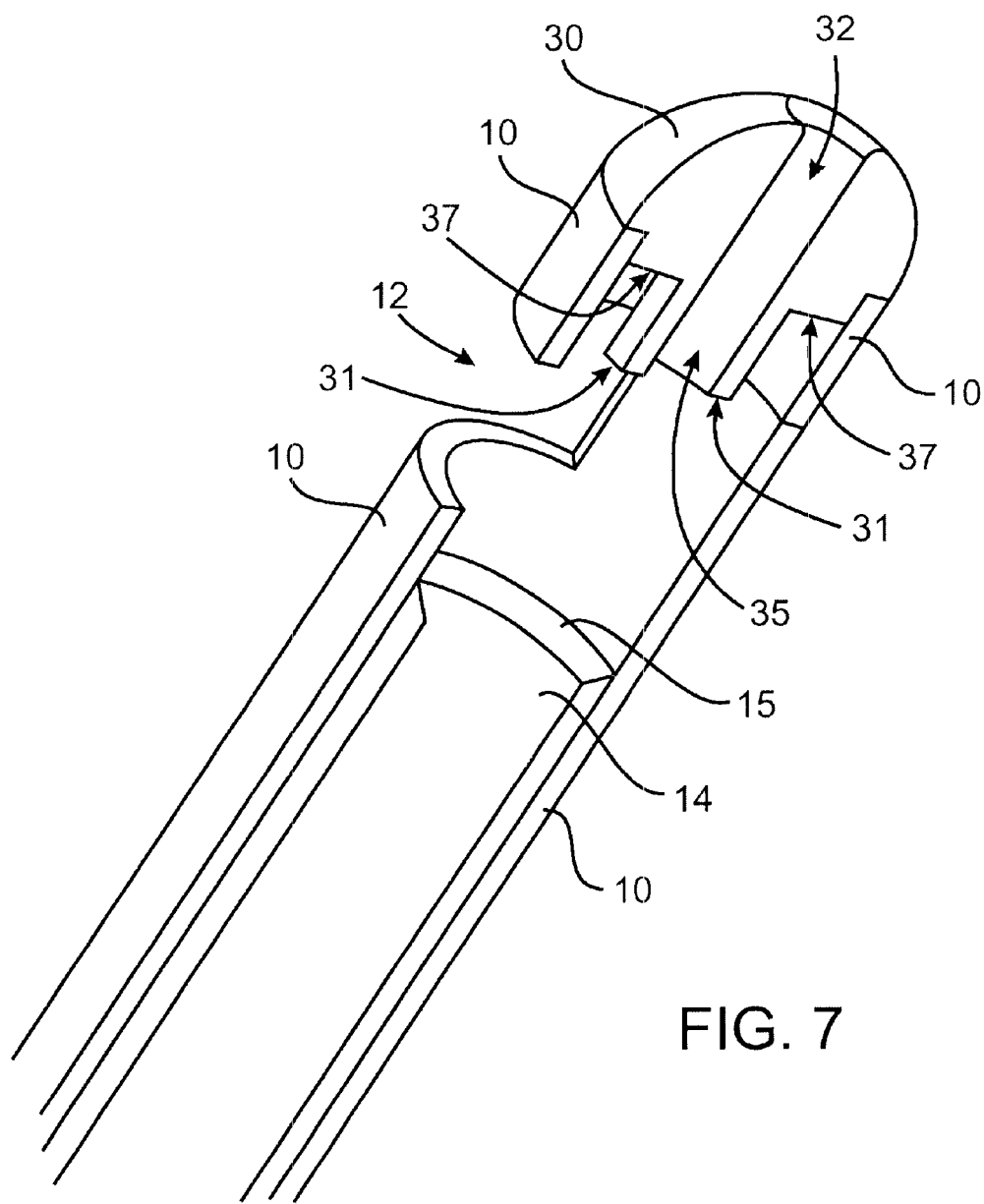
FIG. 7 is a sectional perspective view of a second embodiment of the present invention in a fully opened position.

Referring to FIG. 7, tubular cutting element 14 is shown retracted such that blade 14 is positioned distally such that side opening 12 fully opened. A distal tip 30 having a distal opening 32 and a proximal opening 35 is disposed on the distal end of tubular element 10. Openings 32 and 35 operate as was described with respect to openings 23 and 25. Distal tip 30 further comprises a flat face 31 at its proximal end, operating in the same manner as was described with respect to flat face 21 of insert 20.

Figure 8:
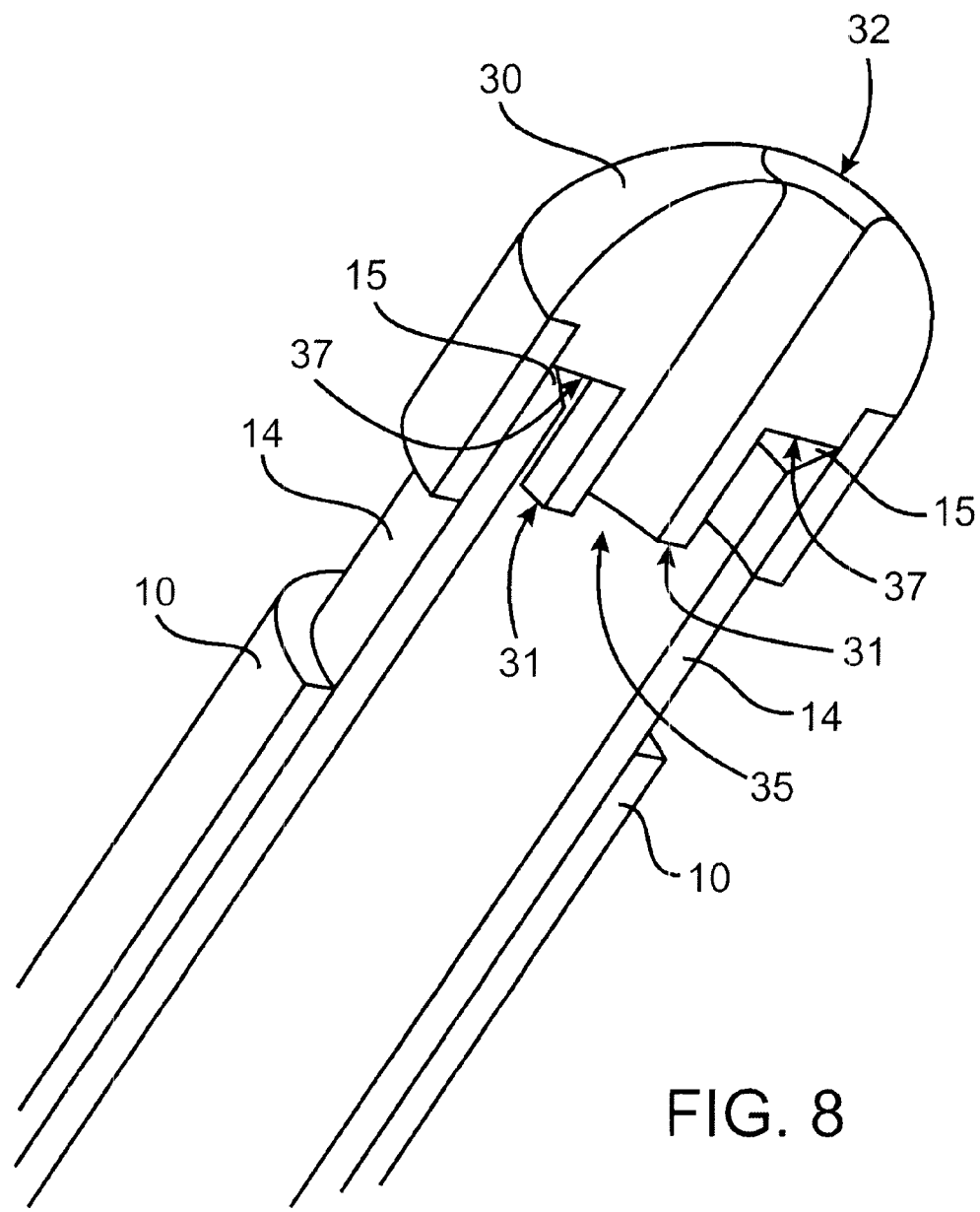
FIG. 8 is a view corresponding to FIG. 7, but with the present invention in a fully closed position.
Figure 9:
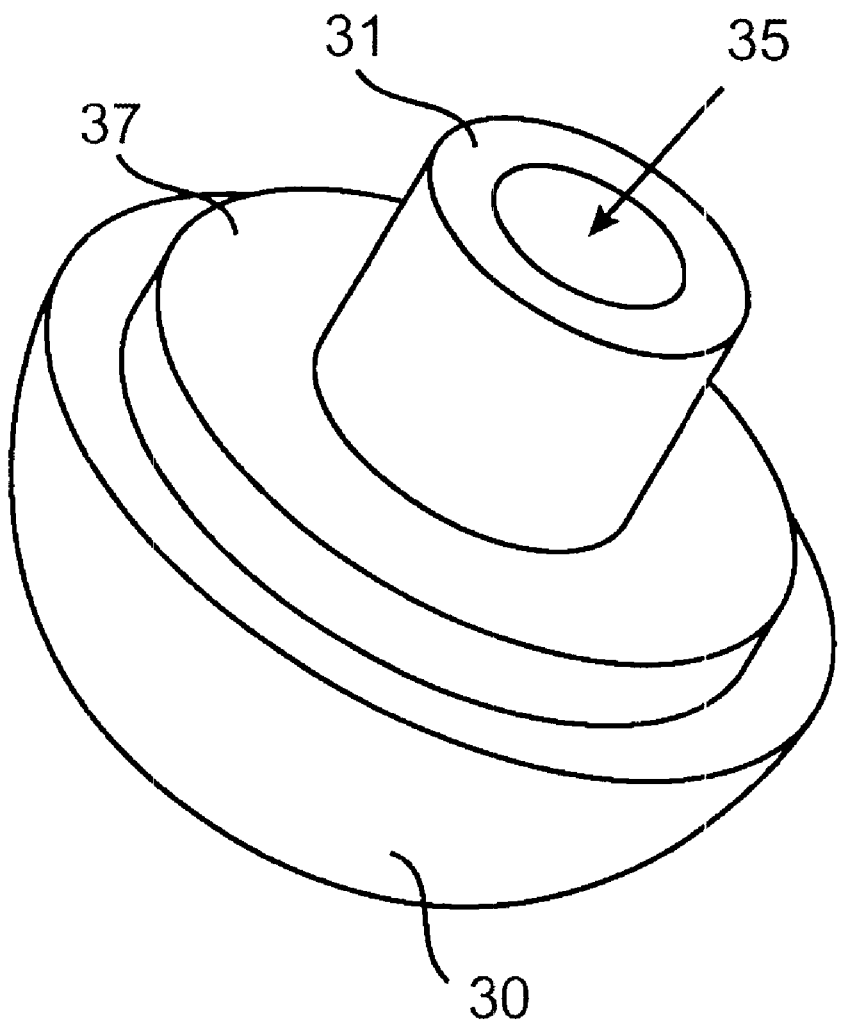
FIG. 9 is a perspective view of the distal tip of the invention shown in FIG. 7.
Figure 10:
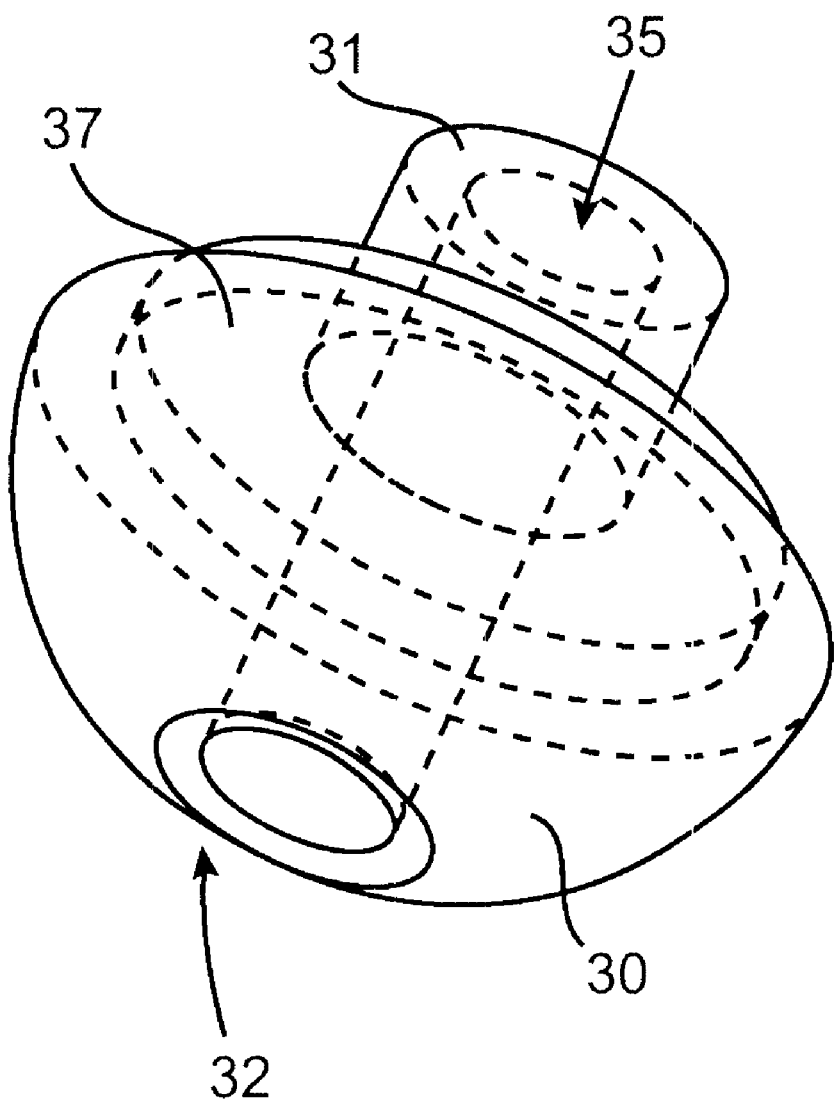
FIG. 10 corresponds to FIG. 9, but shows inner details in phantom.
Figure 11:
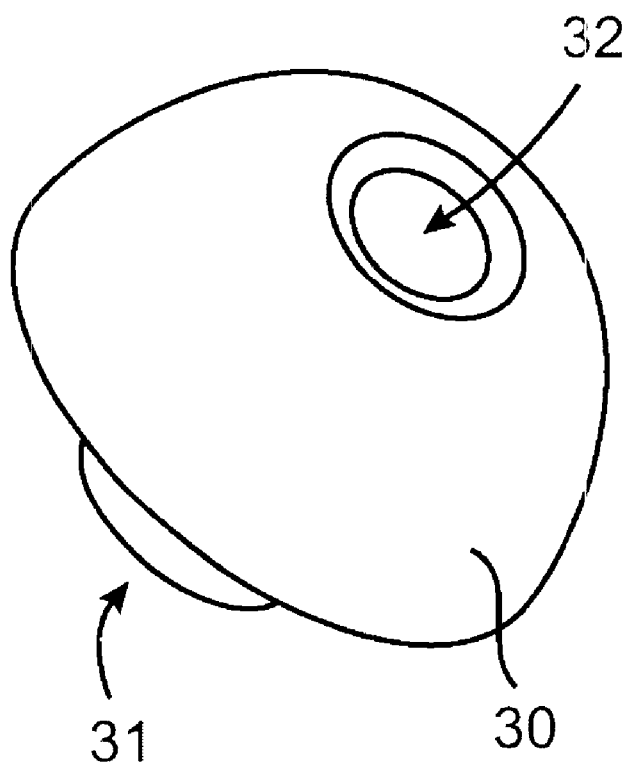
FIG. 11 is a perspective end view of the distal tip of FIGS. 9 and 10.

In addition, distal tip 30 further comprises an annular seating surface 37 against which blade 15 contacts when fully moved to a distal position, (as is shown in FIG. 8). Referring to FIG. 8, the present invention is shown in a fully closed position. Having blade 15 contacting against flat annular seating surface 37, the present invention provides a system of fully cutting away any tissue received through side opening 12. As such, the present invention advantageously does not become jammed or clogged with partially cut away tissue.

While the exemplary embodiments have been described in some detail, by way of example and for clarity of understanding, a variety changes, adaptations, and modifications will be obvious to those of skill in the art. Hence, the scope of the present invention is limited solely by the appended claims.

What is claimed is:

1. A system for successively removing cut tissue from the inner bore of a surgical rongeur or suction punch, comprising:

an elongated tubular member having an inner bore of substantially uniform diameter and a side hole positioned adjacent its distal end for receiving tissue therethrough;

a tubular cutting element having a blade at its distal end, said tubular cutting element being axially moveable within said elongated tubular member to cut tissue extending through said side hole of said elongated tubular member;

a hollow tube extending inwardly from the distal end of said elongated tubular member within the inner bore of said elongated tubular member such that the proximal end of the hollow tube is disposed substantially adjacent the side hole of the elongated tubular member, said hollow tube permitting air and fluid passage therethrough to prevent the formation of a vacuum within the inner bore when said cutting element blocks said side hole of said elongated tubular member while cutting tissue; and a source for suctioning cut tissue from the inner bore of the elongated tubular member.

2. The system of claim 1, wherein the hollow tube has a flat proximal end disposed perpendicular to the longitudinal axis of the elongated tubular member, said flat proximal end having sufficient surface area to maintain cut tissue in a stationary position relative to said elongated tubular element while said tubular cutting element is advanced distally, thereby pushing said cut tissue proximally into said tubular cutting element.

3. The system of claim 1, wherein the hollow tube has an inner bore which is dimensioned narrowly enough such that air and fluid passing therethrough prevents a vacuum from forming in the inner bore of the surgical rongeur or suction punch, yet is dimensioned wide enough such that a sufficient suction force can be continuously maintained in the inner bore of the elongated tubular member.

4. The system of claim 1 and further, wherein the source for suctioning comprises a suction system adapted to reduce the air and fluid pressure within the inner bore of the surgical rongeur or suction punch.

5. A system for successively removing cut tissue from the inner bore of a surgical rongeur or suction punch, comprising:

an elongated tubular member having an inner bore of substantially uniform diameter, a side hole positioned adjacent its distal end, and a hollow tubular portion, said hollow tubular portion projecting inwardly from the distal end such that the proximal end of the hollow tubular portion is disposed substantially adjacent the side hole of the elongated tubular member;

a tubular cutting element having a blade at its distal end, said tubular cutting element being axially moveable within said elongated tubular member to cut tissue extending through said side hole of said elongated tubular member, wherein said hollow tubular portion permits air and fluid passage therethrough to prevent the formation of a vacuum within the inner bore when said cutting element blocks said side hole of said elongated tubular member while cutting tissue; and a source for suctioning cut tissue from the inner bore of the elongated tubular member.

6. The system of claim 5, wherein the hollow tubular portion has a flat proximal end disposed perpendicular to the longitudinal axis of the elongated tubular member.

7. The system of claim 5, wherein the hollow tubular portion has an inner bore which is dimensioned narrowly enough such that air and fluid passing therethrough prevents a vacuum from forming in the inner bore of the surgical rongeur or suction punch, yet is dimensioned wide enough such that a sufficient suction force can be continuously maintained in the inner bore of the elongated tabular member.

8. The system of claim 5 and further, wherein the source for suctioning comprises a suction system adapted to reduce the air and fluid pressure within the inner bore of the surgical rongeur or suction punch.

9. A system for successively removing cut tissue from the inner bore of a surgical rongeur or suction punch, comprising:

an elongated tubular member having a distal end, a side hole positioned adjacent the distal end, and an orifice passing through the distal end;

a tubular cutting element having a blade at its distal end, said tubular cutting element being axially moveable within said elongated tubular member;

a distal tip received within the orifice passing through the distal end of the elongated tubular member, the distal tip projecting inwardly from the distal end of the tubular member into the inner bore of the tubular member to a distance such that the proximal end of the distal tip is disposed adjacent the side hole of the elongated tubular member, wherein the distal tip comprises a hollow tubular portion permitting air and fluid passage therethrough, and wherein the distal tip has a seating surface against which the blade seats when the tubular cutting element is disposed a fully extended distal position, in which the side hole is closed; and a suction source for suctioning cut tissue from the inner bore of the elongated tubular member.

\* \* \* \* \*